(12) United States Patent
Kawai et al.

(10) Patent No.: US 6,303,635 B1
(45) Date of Patent: Oct. 16, 2001

(54) THROMBOLYTIC DRUG

(75) Inventors: Yohko Kawai; Kiyoaki Watanabe, both of Tokyo; Hideaki Kihara, Kawasaki; Hiroshi Yamamoto, Kawasaki; Ryota Yoshimoto, Kawasaki, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/384,214

(22) Filed: Aug. 27, 1999

Related U.S. Application Data

(63) Continuation of application No. PCT/JP98/00737, filed on Feb. 24, 1998.

(30) Foreign Application Priority Data

Feb. 27, 1997 (JP) .................................................. 9-043706
Feb. 27, 1997 (JP) .................................................. 9-043707

(51) Int. Cl.$^7$ .............................................. A61K 31/445
(52) U.S. Cl. ................................................. 514/325
(58) Field of Search .............................................. 514/325

(56) References Cited

U.S. PATENT DOCUMENTS 5,932,593 * 8/1999 Makino et al. ...................... 514/316

FOREIGN PATENT DOCUMENTS 52-87177   7/1977   (JP) .
8-3135     1/1996   (JP) .

OTHER PUBLICATIONS

Minsker, D. et al, "Inhibition of Platelet Aggregation by Cyproheptadine" Platelets Thromb. Proc. Symp. Meeting Date 1972, 1974 pp. 161–176, X000973564.

Nowak, G. et al, Influence of Cyproheptadine on Endotoxin–Induced Disseminated Intravascular Coagulation (DIC) in Weaned Pigs), Thrombosis and Haemostasis, 1985, pp. 252–254, XP000973507.

Larry R. Bush, "Effects of the Serotonin Antagonists, Cyproheptadine, Ketanserin and Mianserin, on Cyclic Flow Reductions in Stenosed Canine Coronary Arteries", The Journal of Pharmacology and Experimental Therapeutics, vol. 240, No. 2, pp. 674–682, 1987.

Minsker, David et al. Inhibition of platelet aggreation by cyproheptadine. Chemical Abstracts vol. 82, 1975, (38511y).*

* cited by examiner

Primary Examiner—Theodore J. Criares
Assistant Examiner—Jennifer Kim
(74) Attorney, Agent, or Firm—Oblon, Spivak, McClelland, Maier & Neustadt, P.C.

(57) ABSTRACT

A thrombolytic drug containing cyproheptadine, a compound of the following formula or a salt thereof as the active ingredient is provided. This thrombolytic drug has a function of accelerating the release of a tissue plasminogen activator (t-PA), while exerting no effect on the release of type-1 plasminogen activator inhibitor (PAI-1) which deactivates t-PA or reducing the release thereof.

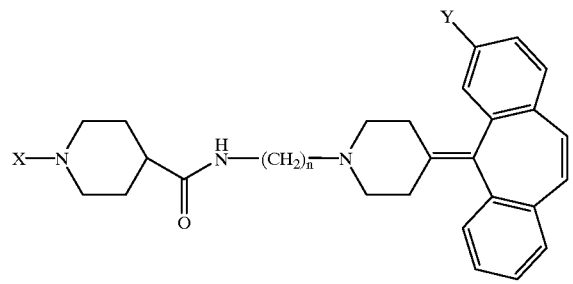

wherein n represents an integer of 2 or 3, Y represents a hydrogen atom or halogen atom, and X represents a formyl group, acetyl group or hydrogen atom.

8 Claims, No Drawings

THROMBOLYTIC DRUG

This application is a continuation of PCT/JP98/00737 filed Feb. 24, 1998.

BACKGROUND OF THE INVENTION

The present invention relates to a thrombolytic drug which can be orally administered. In particular, the present invention relates to a thrombolytic drug having a function of accelerating the release of a tissue plasminogen activator (t-PA) in vascular endothelial cells, while exerting substantially no effect on the release of type-1 plasminogen activator inhibitor (PAI-1) which deactivates t-PA or reducing the release thereof.

A thrombosis caused by the blood coagulation in the bodies causes serious diseases such as hypertension, stroke and myocardial infarction. Usually drugs affecting the blood such as antiplatelet drugs, anticoagulant drugs and thrombolytic drugs are used for these diseases. Although the antiplatelet drugs and anticoagulant drugs are effective in preventing the formation of thrombi, the effects of them on the patients having the thrombi already formed are only slight and an early fibrinolytic therapy with a thrombolytic drug is necessitated. In the fibrinolytic therapy, a factor capable of developing a fibrinolytic reaction is given in order to dissolve and thereby to remove the thrombi. As the thrombolytic agents, those obtained from fibrinolytic substances per se such as tissue plasminogen activators, urokinase, streptokinase and prourokinase by a gene recombination technique have been used hitherto. However, such a thrombolytic agent must be directly applied to a location of the thrombus formation or the blood vessel. Under these circumstances, the development of a thrombolytic drug which can be orally administered has been demanded.

DISCLOSURE OF THE INVENTION

The object of the present invention is to provide an oral thrombolytic drug having a function of accelerating the release of a tissue plasminogen activator (t-PA) in vascular endothelial cells, while exerting substantially no effect on the release of type-1 plasminogen activator inhibitor (PAI-1) which deactivates t-PA or reducing the release thereof.

This and other objects of the invention will be apparent from the following description and Examples.

After intensive investigations, the inventors have found that cyproheptadine known as an antihistaminic agent or antiserotonergic agent and specified piperidine derivatives known as serotonin antagonists or antiplatelet agents [Japanese Patent Unexamined Published Application (hereinafter referred to as "J. P. KOKAI") No. Hei 8-3135] have functions of accelerating the release of t-PA from the vascular endothelial cells and reducing the release of PAI-1 which deactivates t-PA and inhibits the fibrinolytic reaction. The present invention has been completed on the basis of this finding.

Namely, the present invention relates a thrombolytic drug containing a compound of the following formula (I) or (II) or a salt thereof as the active ingredient:

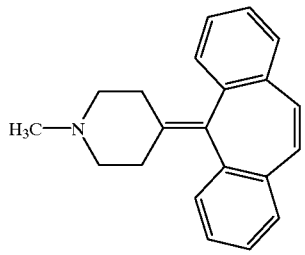

(I)

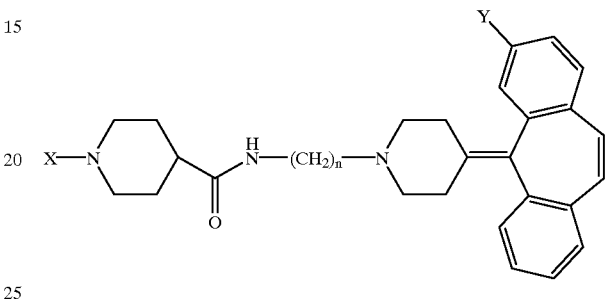

(II)

wherein n represents an integer of 2 or 3, Y represents a hydrogen atom or halogen atom, and X represents a formyl group, acetyl group or hydrogen atom.

BEST MODE FOR CARRYING OUT THE INVENTION

Cyproheptadine of above formula (I) is a known compound having antiserotonergic effect, antihistaminic effect, atropine-like effect, etc., and mentioned in Japanese pharmacopoeia C-587. This compound is easily available on the market as, for example, Periactin (registered trade name of an antihistaminic agent of Banyu Pharmaceutical Co., Ltd.) or cyproheptadine hydrochloride (a compound of Sigma Co.).

The piperidine derivatives of above formula (II) are well-known compounds. They can be easily produced by a well-known process such as that described in J. P. KOKAI No. Hei 8-3135. Reaction scheme I shows an example of the production processes. Di-t-butyl dicarbonate (2) is reacted with 2-aminoethyl bromide hydrobromide (3) in the presence of sodium hydrogencarbonate to obtain N-t-butoxycarbonyl-2-bromoethylamine (4). This compound (4) is condensed with 4-(5H-dibenzo[a,d]cycloheptene-5-ylidene)piperidine (5) in the presence of a base such as triethylamine to obtain 4-(5H-dibenzo[a,d]cycloheptene-5-ylidene)-1-(2-t-butoxycarbonylamino)ethyl)piperidine (6). This compound (6) is condensed with a compound (7), from which t-butoxycarbonyl group has been removed with 4 M hydrochloric acid/dioxane, and 1-formylisonipecotic acid (8) in the presence of a condensing agent such as 1-(3-dimethylaminopropyl)-3-ethylcarbodiimide to obtain 1-formyl-N-(2-(4-(5H-dibenzo[a,d]cycloheptene-5-ylidene)-1-piperidinyl))ethylisonipecotic acid amide (9).

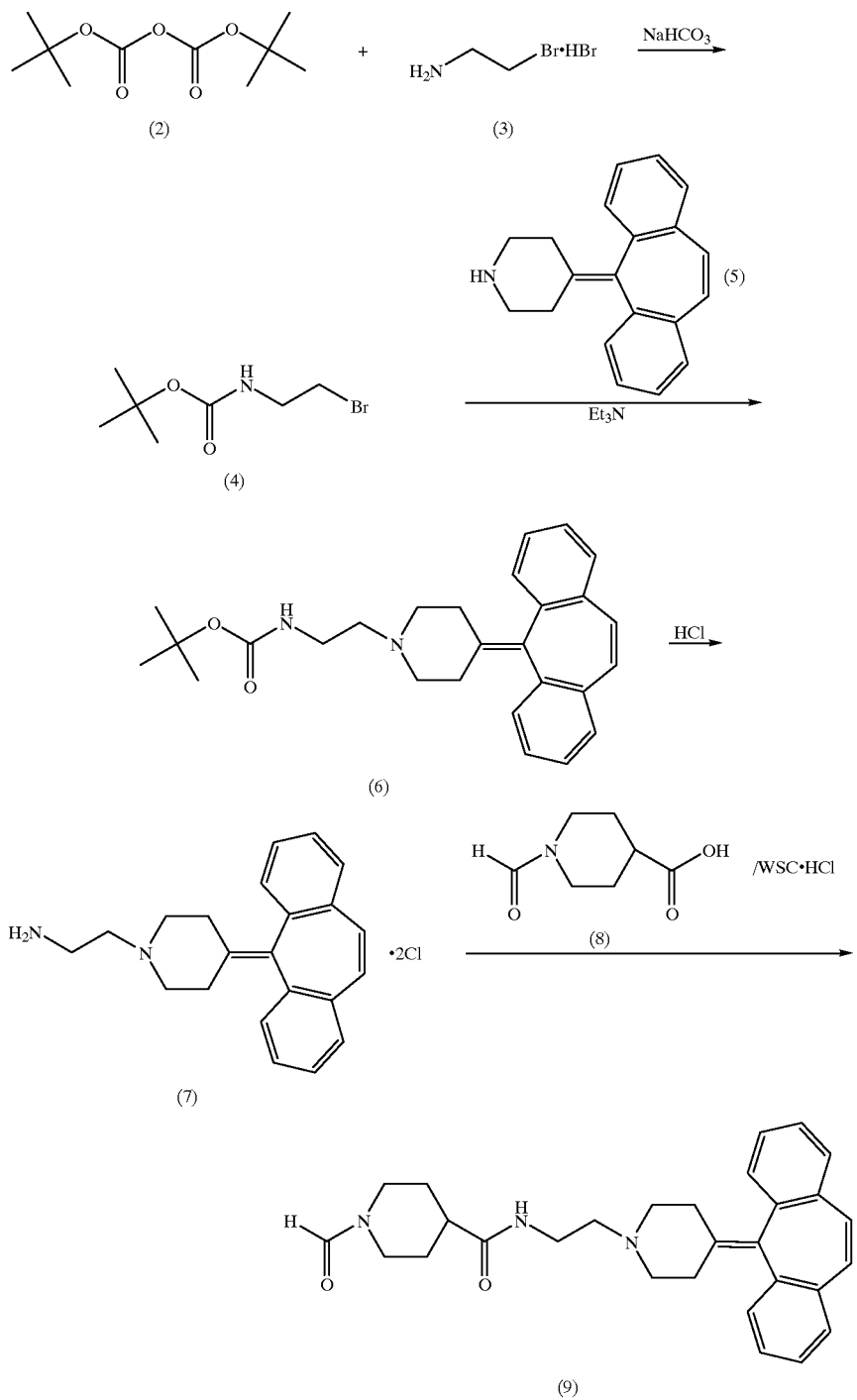

Among the compounds of formula (II), a compound wherein n is 2, Y is hydrogen atom and X is formyl group is preferred.

The reaction product thus obtained by the above-described process is isolated in the form of the free compound or it can be treated by an ordinary salt-forming process, and isolated in the form of a salt. The isolation can be conducted by an ordinary technique such as extraction, concentration, evaporation, crystallization or any of various chromatographic methods.

The salts of the compounds of the above formulae (I) and (II) include acid-addition salts thereof with inorganic acids such as hydrochloric acid, hydrobromic acid, sulfuric acid, nitric acid, phosphoric acid and carbonic acid and also organic acids such as formic acid, acetic acid, lactic acid, salicylic acid, mandelic acid, citric acid, oxalic acid, maleic acid, fumaric acid, tartaric acid, tannic acid, malic acid, p-toluenesulfonic acid, methanesulfonic acid and benzenesulfonic acid.

The compound of formula (I) or its salt has a function of accelerating the release of t-PA, while exerting substantially no influence on the release of PAI-1 which deactivates t-PA or reducing the release thereof and, therefore, it is useful as a thrombolytic agent in the fibrinolytic therapy.

The compound of formula (II) or its salt has a function of specifically accelerating the release of t-PA, while exerting substantially no influence on the release of PAI-1 which deactivates t-PA and, therefore, it is useful as a thrombolytic agent in the fibrinolytic therapy.

The dosage forms of the thrombolytic drug containing the compound of formula (I) or (II) or its salt as the active ingredient are ordinary ones such as tablets, powder, pills, granules, sugar-coated tablets, emulsion, capsules, solution, parenteral solution and suppositories. Those products can be prepared by using a carrier, filler and other preparation adjuvants in an ordinary manner.

When the compound of formula (I) or (II) or salt thereof is used as the thrombolytic agent, it can be administered either orally or parenterally. The dose, which varies depending on the age, body weight, conditions and administration method, is about 0.1 to 500 mg/day, preferably 1 to 50 mg/day, for adults in the oral administration and 0.01 to 100 mg/day, preferably 0.1 to 10 mg/day, in the parenteral administration.

The compound of formula (I) or (II) or salt thereof directly acts on the vascular endothelial cells to specifically accelerate the release of the t-PA having the thrombolytic function. Thus, such a compound is useful in the thrombolytic therapy against the thrombosis.

The following Examples will further illustrate the present invention, which by no means limit the invention.

EXAMPLE 1

Test on the Release of t-PA From Human Endothelial Cells

Human vascular endothelial cells were cultured by a modified method of Jaffe et al. In this method, human umbilical vein endothelial cells were isolated with collagenase (a product of Nitta Gelatin Inc.). Then, these cells were cultured in M 199 medium (a product of Gibco Laboratories) containing 10% heat inactivated fetal calf serum (a product of Seromex Vilshofen), 30 μg/ml of Endothelial Cell Growth Supplement (a product of Collaborative Res. Inc.,) and 6 U/ml of heparin in a culture flask coated with gelatin in a $CO_2$ incubator at 37° C. The human vascular endothelial cells were obtained from the culture flask by trypsin/EDTA (a product of Gibco Laboratories) treatment, and further cultured on a 35 mm petri dish pre-coated with 300 μg/ml of collagen type IV (a product of Iwaki Glass Co., Ltd.). The cells which had become the confluent in the second passage were used for the determination test. A test compound was added to the cells on the petri dish. After the incubation for 24 hours, the quantity of t-PA antigen released in the supernatant culture liquid was determined by the enzyme immunoassay by the double antibody technique with Imulyse TM t-PA kit (a product of Biopool AB). The quantity of the released t-PA antigen was calculated on the basis of the quantity (100%) of t-PA antigen released in the absence of the test compound. The results are shown in Table 1.

EXAMPLE 2

Test on the Release of PAI-1 From Human Endothelial Cells

Human vascular endothelial cells were cultured by a modified method of Jaffe et al. In this method, human umbilical vein endothelial cells were isolated with collagenase (a product of Nitta Gelatin Inc.). Then, these cells were cultured in M 199 medium (a product of Gibco Laboratories) containing 10% heat inactivated fetal calf serum (a product of Seromex Vilshofen), 30 μg/ml of Endothelial Cell Growth Supplement (a product of Collaborative Res. Inc.,) and 6 U/ml of heparin in a culture flask coated with gelatin in a $CO_2$ incubator at 37° C. The human vascular endothelial cells were obtained from the culture flask by trypsin/EDTA (a product of Gibco Laboratories) treatment, and further cultured on a 35 mm petri dish pre-coated with 300 μg/ml of collagen type IV (a product of Iwaki Glass Co., Ltd.). The cells which had become the confluent in the second passage were used for the determination test. A test compound was added to the cells on the petri dish. After the incubation for 24 hours, the quantity of PAI-1 antigen released in the supernatant culture liquid was determined by the enzyme immunoassay by the double antibody technique with TintElize PMI-1 kit (a product of Biopool AB). The quantity of the released t-PA antigen was calculated on the basis of the quantity (100%) of t-PA antigen released in the absence of the test compound. The results are shown in Table 1.

TABLE 1

| Compound | Concentration of compound [μM] | Amount of released t-PA[%] | Amount of released PAI-1[%] |
| --- | --- | --- | --- |
| 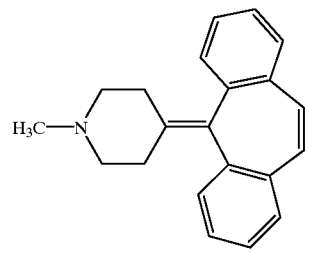 | 100 | 171 | 92 |
| 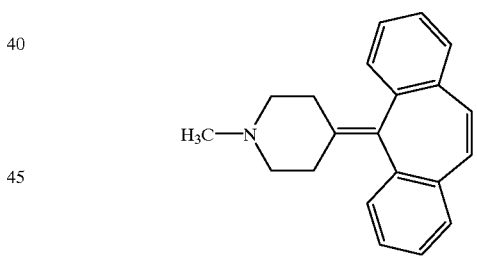 | | | |

In Table 1, the amount of released t-PA and that of released PMI-1 were the averages of the results of the experiments each conducted three times.

It is apparent from Table 1 that cyproheptadine accelerates the release of t-PA and reduces the release of PAI-1 which deactivates t-PA.

EXAMPLE 3

The test on the release of t-PA from human endothelial cells and the test on the determination of release of PAI-1 from human endothelial cells were conducted in the same manner as that of Examples 1 and 2, respectively, except that a compound shown in Table 2 was used as the test compound and that the incubation was conducted in the presence of 1000 U/ml of a tumor necrosis factor (TNF α) applied to the cells on the petri dish together with the test compound. The results are shown in Table 2.

TABLE 2

| Compound | Concentration of compound [μM] | Amount of released t-PA [ng/ml] | Amount of released PAI-1 [ng/ml] |
|---|---|---|---|
| 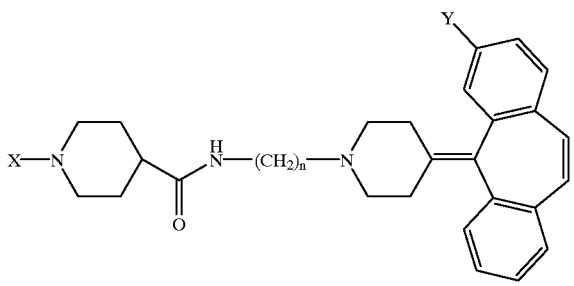 ·HCl·H$_2$O | 0 | 9 (100%) | 1950 (100%) |
| | 20 | 11 (122%) | 2010 (103%) |
| | 100 | 12 (133%) | 1940 (99%) |
| | 500 | 25 (277%) | 1980 (102%) |

In Table 2, the amount of released t-PA and that of released PAI-1 were the averages of the results of the experiments each conducted three times. The values in Table 2 were those obtained by the actual measurement and the values in the parentheses were those calculated on the basis of the values (100%) obtained in the absence of the test compound.

It is apparent from Table 2 that the compounds of formula (II) accelerates the release of t-PA and that they exert substantially no influence on the release of t-PA and that they exert substantially no influence on the release of PAI-1 which deactivates t-PA.

What is claimed is:

1. A method for dissolving blood clots, which comprises: administering to a patient having a blood clot an amount effective to dissolve said blood clot of a compound of formula (I) or (II) or a salt thereof having a function of accelerating the release of a tissue plasminogen activator in vascular endothelial cells while exerting substantially no effect on the release of type-1 plasminogen activator inhibitor:

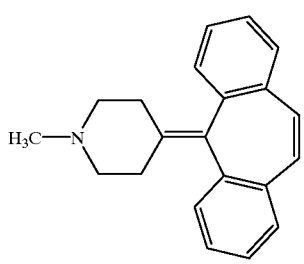

(I)

-continued (II)

wherein n represents an integer of 2 or 3, Y represents a hydrogen atom or halogen atom, and X represents a formyl group, acetyl group or hydrogen atom.

2. The method of claim 1, wherein the active ingredient is the compound of formula (I) or salt thereof.

3. The method of claim 1, wherein the active ingredient is a compound of formula (II) or a salt thereof.

4. The method of claim 3, wherein n in the formula is 2, Y is a hydrogen atom and X is a formyl group.

5. The method of claim 1, wherein the compound of formula (I) or (II) contains a carrier and/or filer.

6. The method of claim 1, wherein the compound of formula (I) or (II) is orally administered.

7. A method for enhancing release of a tissue plasminogen activator in a patient having blood clots, comprising:

administering a compound of formula (I) or (II) or a salt thereof having a function of accelerating the release of a tissue plasminogen activator in vascular endothelial cells while exerting substantially no effect on the release of type-1 plasminogen activator inhibitor

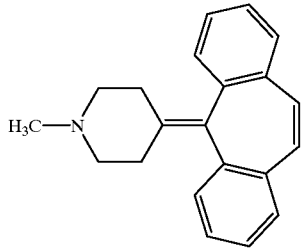
(I)

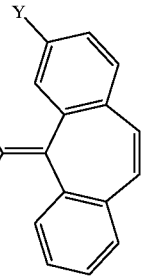
(II)

wherein n represents an integer of 2 or 3, Y represents a hydrogen atom or halogen atom, and X represents a formyl group, acetyl group or hydrogen atom, in an amount effective to enhance the release of a tissue plasminogen activator.

8. The method of claim 7, wherein the active ingredient is orally administered.

* * * * *